United States Patent
Kinney

(10) Patent No.: US 11,801,339 B2
(45) Date of Patent: Oct. 31, 2023

(54) SYRINGE AND TUBE HOLDER

(71) Applicant: Nicholas Howard Kinney, De Pere, WI (US)

(72) Inventor: Nicholas Howard Kinney, De Pere, WI (US)

( * ) Notice: Subject to any disclaimer, the term of this patent is extended or adjusted under 35 U.S.C. 154(b) by 45 days.

(21) Appl. No.: 17/649,090

(22) Filed: Jan. 27, 2022

(65) Prior Publication Data
US 2023/0233753 A1 Jul. 27, 2023

(51) Int. Cl.
*A61M 5/00* (2006.01)

(52) U.S. Cl.
CPC ........ *A61M 5/008* (2013.01); *A61M 2209/082* (2013.01)

(58) Field of Classification Search
CPC .................. A61M 5/008; A61M 2209/082
USPC ............................... 248/56, 51, 50; 206/570
See application file for complete search history.

(56) References Cited

U.S. PATENT DOCUMENTS

| | | | | |
|---|---|---|---|---|
| 2,313,905 A | * | 3/1943 | Wallin | A61M 5/008 211/60.1 |
| 2,371,433 A | * | 3/1945 | Davis | B25H 3/04 211/94.01 |
| 2,659,485 A | * | 11/1953 | Duley | A61M 5/008 206/564 |
| D267,744 S | * | 1/1983 | Flynn | D24/229 |
| D354,874 S | * | 1/1995 | Burch | D6/567 |
| 5,478,332 A | * | 12/1995 | Stockwell | A61M 25/02 604/533 |
| 5,531,702 A | * | 7/1996 | Baker | A61M 5/008 211/85.13 |
| 5,704,495 A | * | 1/1998 | Bale | A61B 50/20 D6/567 |
| D424,692 S | * | 5/2000 | Monaghan | D24/128 |
| 6,193,932 B1 | * | 2/2001 | Wu | A61L 2/07 206/439 |
| 6,955,259 B1 | * | 10/2005 | Jesse | A61M 5/008 206/370 |
| 6,969,498 B1 | * | 11/2005 | Riley | A61B 50/20 206/370 |
| 7,229,051 B2 | * | 6/2007 | Mailhot, Jr. | F16L 3/1218 248/205.2 |
| 2002/0014560 A1 | * | 2/2002 | Diamond | A61B 50/24 248/37.3 |
| 2016/0000993 A1 | * | 1/2016 | Endyk | A61M 5/1782 211/85.13 |

* cited by examiner

*Primary Examiner* — Kimberly T Wood
(74) *Attorney, Agent, or Firm* — Dunlap Bennett & Ludwig, PLLC

(57) ABSTRACT

A syringe and tube organizer having a mounting plate for connecting to a supporting surface and a holder plate extending from the mounting plate. The holder plate may provide one syringe-receiving opening and a plurality of tube receiving slots. The tube receiving slots are defined by a void slot having a retention detent, and wherein the void slot terminates at the center of a spherical cap void.

6 Claims, 3 Drawing Sheets

SYRINGE AND TUBE HOLDER

BACKGROUND OF THE INVENTION

The present invention relates to retaining devices for and, more particularly, an organizer for extension tubes and syringes.

Syringes and extension tubes are mainstays of many procedures, including childcare and medical applications. One problem that results from their ubiquity, though, is that having a lot of extension tubes and/or one or more syringes on one's plate or tray can result in a disorganized jumble that, slows down their (possibly critical) application. Even in the absence of an existential threat or a time crunch, almost all users and practitioners can benefit from simplification and organization of the tools of their trade. Current retaining devices that are used for syringes and extension tubes do not work well because they are inefficient as they leave such equipment mixed with other items. In the case where the user is a caretaker, these critical pieces of equipment can get lost among random kitchen items, which can increase the stress of the caretaker if they are in a pinch.

As can be seen, there is a need for an organizer for extension tubes and syringes, wherein the organizer is wall mountable for easy accessibility and visibility.

The present invention gives the user the ability to organize their extension tubes and syringes; specifically, the organizer of the present invention provides a holder plate or palette that extends orthogonally from a wall mounting plate, wherein the palette provides a plurality of radial slots communicating to its perimetral edge. Each slot may contain a protrusion that holds flexible extension tubes therein without letting it fall out. The palette also provides a syringe-retaining opening for removably receiving the cylindrical portion of the syringe.

The present invention helps caregivers of infants because most items used to administer deliverables to a g-tube infant need to be washed and dried. These items can now be put into a single place out of the other household items. Beyond that, the present invention helps the user simplify steps in their day-to-day life. If one were able to organize a few special items wherever it is needed, then this is what the present invention was designed for.

SUMMARY OF THE INVENTION

In one aspect of the present invention, a syringe and tube organize includes the following: a mounting plate; a holding plate extending approximately orthogonally from the mounting plate; a syringe-receiving opening defined by the holding plate; and a plurality of tube slots radially extending from a perimetral edge of the holding plate, wherein each tube slot terminates at or near a center of a divot in the holding plate.

In another aspect of the present invention, the above syringe and tube organizer further includes wherein each divot is defined by a mathematical spherical cap cutout from an upper surface of the holding plate, wherein each tube slot has a retention detent between the perimetral edge and the divot, wherein each retention detent is approximately midway between the perimetral edge and the divot, wherein the tube slot is linear, wherein the syringe-receiving opening is defined by a head portion, a neck portion, and a shoulder portion, wherein the should portion is opposing chamfers connecting the neck portion and the perimetral edge, wherein the opposing chamfers are 45 degrees; and including a connector along a surface of the mounting plate opposite the holding plate, wherein the plurality of tube slots comprising two tube slots on each side of the syringe-receiving opening, wherein the syringe-receiving opening is centrally disposed along the holding plate.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, an embodiment of the present invention provides a syringe and tube organizer having a mounting plate for connecting to a supporting surface and a holder plate extending from the mounting plate. The holder plate may provide one syringe-receiving opening and a plurality of tube receiving slots. The tube receiving slots are defined by a void slot having a retention detent, and wherein the void slot terminates at the center of a spherical cap void.

Referring now to FIGS. 1 through 6, the present invention may include a syringe and tube organizer 100. The organizer 100 has a mounting plate 10 for connecting to a supporting surface 24, such as a vertical surface or wall. A connection element 26 may removably attached a rear side of the mounting plate 10 to the supporting surface 24. The connection element 26 may be adhesive, glue, a bonding agent, or any fastener that enables connecting one object to another as contemplated herein.

Figure 3:
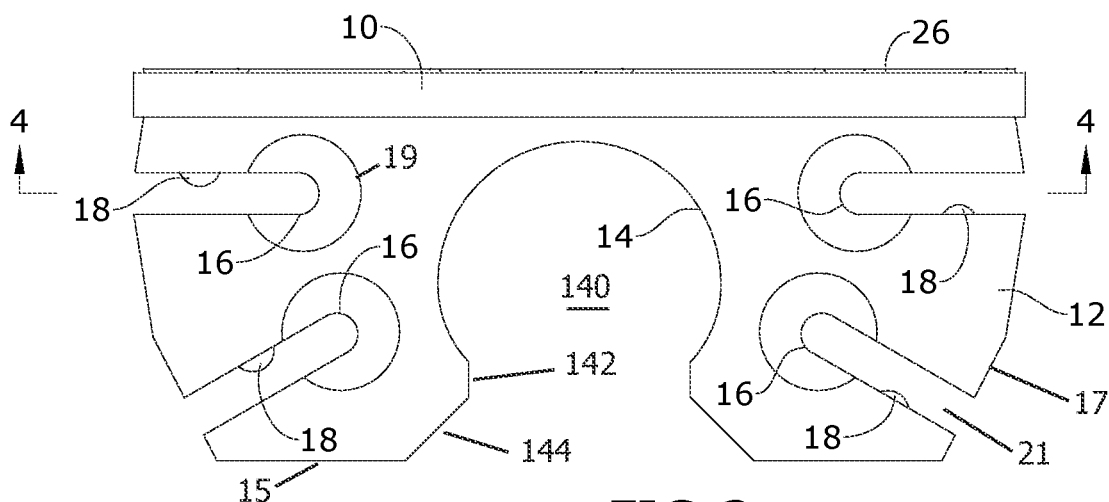
FIG. 3 is a top plan view of an exemplary embodiment of the present invention.
Figure 4:
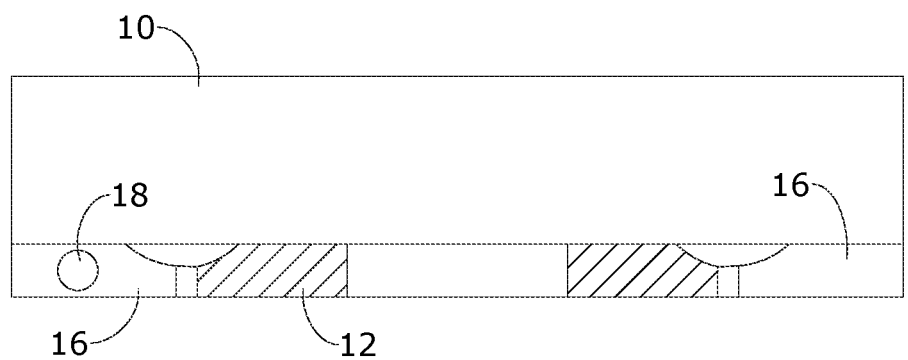
FIG. 4 is a section view of an exemplary embodiment of the present invention, taken along line 4-4 of FIG. 3.

The organizer 100 may have a palette or holder plate 12 extending forward from and approximately orthogonal relative to the mounting plate 10. The holder plate 12 may have a centrally disposed syringe-receiving opening 140 defined by a curvilinear edge 14 (or 'head portion'), a linear transition 142 (or 'neck portion'), and chamfer 144 (or 'shoulder portion') between the neck portion and a frontal edge 15 of the holder plate 12, as illustrated in FIG. 3. The syringe-receiving opening 140 is dimensioned to slidably receive the cylindrical portion of a syringe 22.

Figure 5:
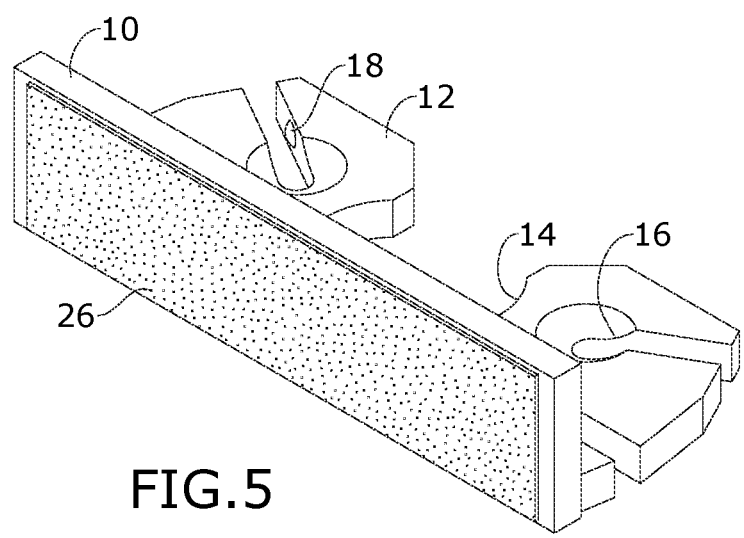
FIG. 5 is a rear perspective view of an exemplary embodiment of the present invention.
Figure 6:
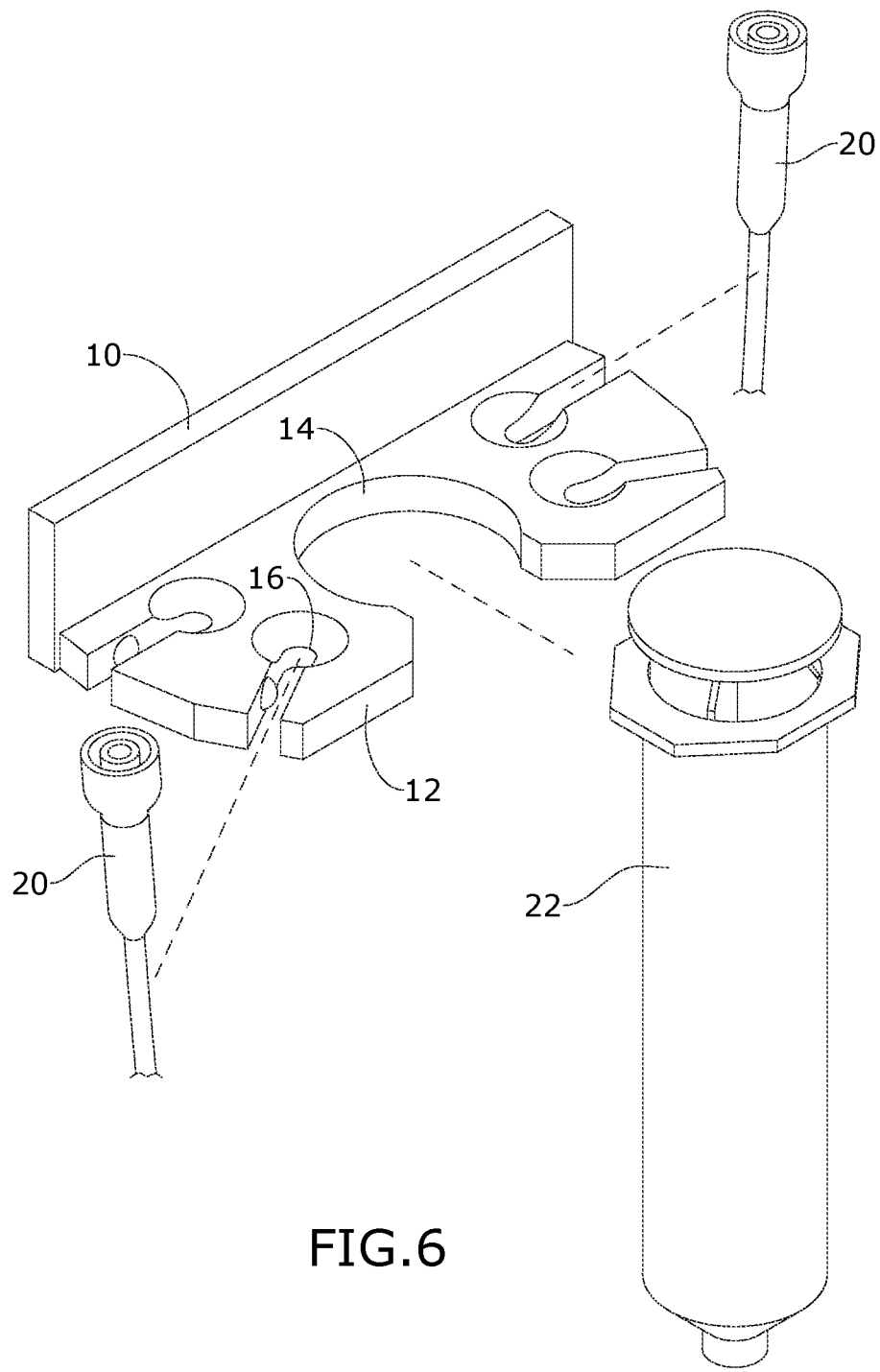
FIG. 6 is an exploded perspective view of an alternative exemplary embodiment of the present invention, illustrating placement of a syringe and two extension tubes in their respective receiving portions of the present invention.

The holder plate 12 may have a plurality of tube slots 16 radially extending inward from a perimetral edge 17 of the holder plate 12, as illustrated in FIG. 3. Each tube slot 16 may have a void slot 21 extending from the perimetral edge 17 and communicating with a divot 19. Each divot 19 may be a spherical cap (void) cut out from the upper surface of the holder plate 12, as illustrated in FIG. 5. The void slot 21 of the tube slot 16 may terminate at the center of the spherical cap (void) and so that portion of the void slot 21 defined by the spherical cap has a dimension approximately equal to the radius (of the base) of the spherical cap. Dimensions of such radius ranges about 15 millimeters (mm) to 30 mm, wherein the height of the spherical cap is less than said radius, approximately 50 to 75 percent thereof. The width of the tube slot 16 (here, the term 'width' being in the opposite direction of its longitudinal length extending from the perimetral edge 17) may be between five mm and nine mm. The retention detent 18 may protrude approximately two to four mm into the tube slot 16, widthwise. The full width of the syringe and tube organizer 100 may be between 80- and 120-mm. The syringe-receiving opening 140 is dimensioned to snugly receive many of the standard sized syringes 22—i.e., the curvilinear edge 14 defines a diameter between 20- and 40-mm, wherein the width of the shoulder portion terminates at a perimetral width of five to 20 percent wider than the diameter defied by the curvilinear edge 14.

Along the void slot 21 may be a retention detent 18 or protrusion extending into the void slot 21 from a sidewall thereof. The retention detent 18 may be disposed approximately midway from the perimetral edge 17 and the divot 19. The void slot 21 is dimensioned and adapted to slidably receive a portion of a tube 20, wherein the tube 20 needs to be urged past the retention detent 18. The retention detent 18 is dimensioned and adapted so that the portion of the tube cannot slide past it along the void slot 21 without intentional urging of the user, thereby preventing unintentional removal of the tube 20. It should be understood that even though the Figures show the void slots 21 as linear, they may be curvilinear, circuitous or the like, as long as they function as disclosed herein.

Figure 1:
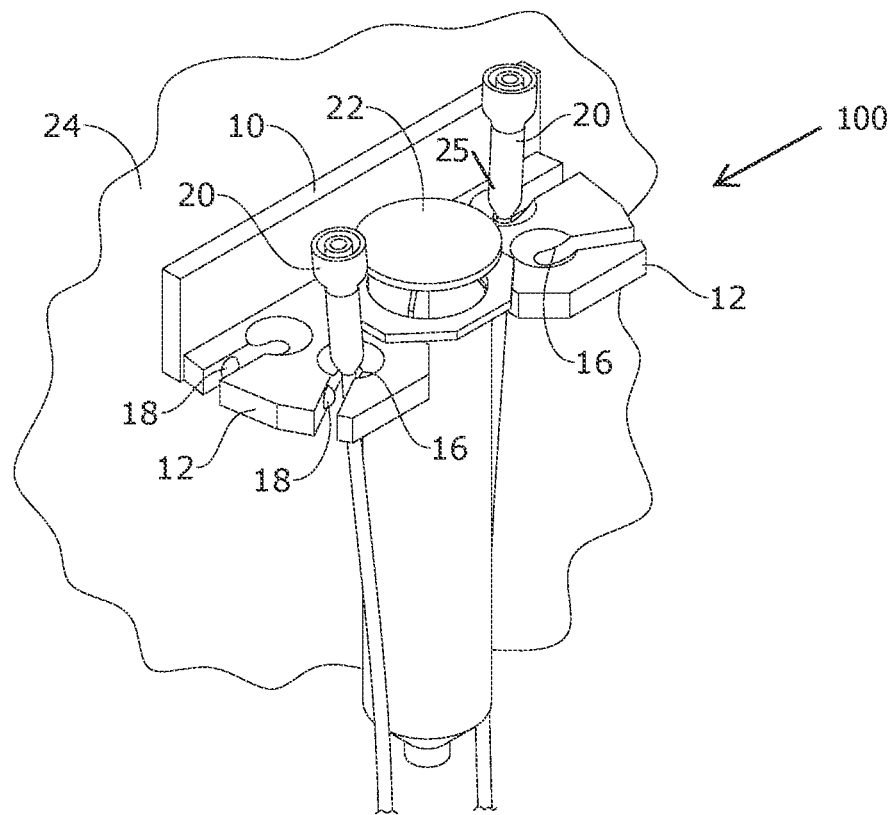
FIG. 1 is a perspective view of an exemplary embodiment of the present invention, shown in use.
Figure 2:
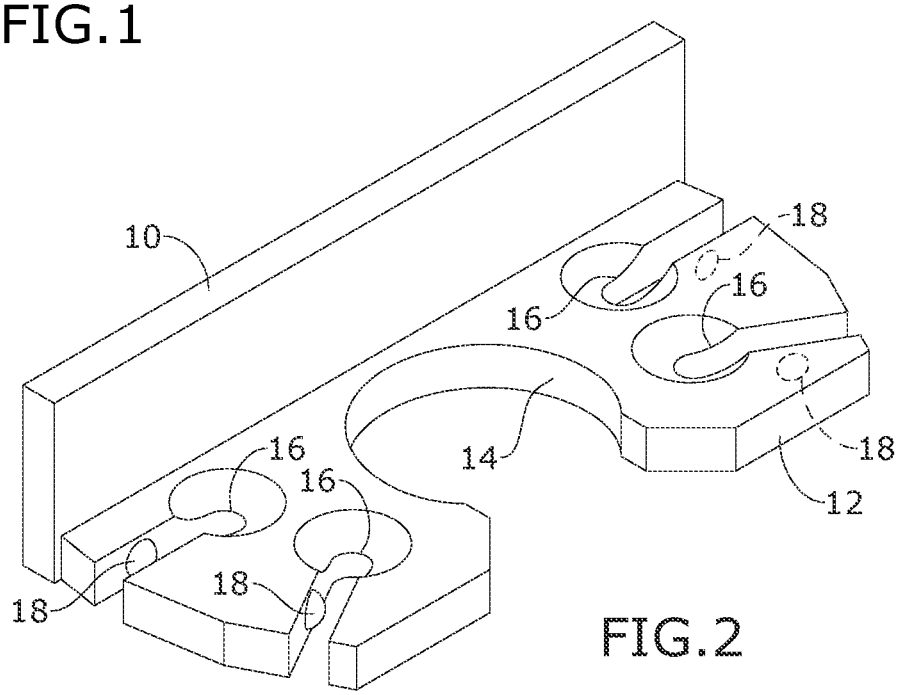
FIG. 2 is a perspective view of an exemplary embodiment of the present invention.

The divots 19 facilitate receipt of the tube 20 as well as operatively associated portions 25 thereof, as illustrated in FIG. 1. Such portions tend to be wider than the tube itself and have a tapered or conical base where it joins to the end of the tube 20. This tapered/conical interface may sit in the divot, facilitating an upright orientation when the extension tube 20 is retrievable stored in the tube slot 16.

A method of using the present invention may include the following. A user may mount, by way of the mounting plate 10, the syringe and tube organizer 100 on a supporting surface 24. Then the user may selectively slide a syringe 22 into the syringe-receiving opening 140 as well as a tube 20 into one or more of the divots 19, by way of the void slots 21, thereby separating and organizing these special items from other items for wherever one or more is needed.

As used in this application, the term "about" or "approximately" may refer to a range of values within plus or minus 10% of the specified number. For instance, approximately orthogonal can include a 81-degree to 99-degree relative angle. And approximately midway may be construed as between 45 and 55 percent along a length.

Generally speaking, recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments.

The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the disclosed embodiments.

In the following description, it is understood that terms such as "first," "second," "top," "bottom," "up," "down," and the like, are words of convenience and are not to be construed as limiting terms unless specifically stated to the contrary.

It should be understood, of course, that the foregoing relates to exemplary embodiments of the invention and that modifications may be made without departing from the spirit and scope of the invention as set forth in the following claims.

What is claimed is:

1. A syringe and tube organizer, comprising:
   a mounting plate;
   a holding plate extending approximately orthogonally from the mounting plate;
   a syringe-receiving opening defined by the holding plate, wherein the syringe-receiving opening is defined by a head portion, a neck portion, and a shoulder portion, wherein the shoulder portion is opposing chamfers connecting the neck portion and a perimetral edge; and
   a plurality of tube slots radially extending from a the edge of the holding plate, wherein each tube slot terminates at or near a center of a divot in the holding plate, wherein each divot is defined by a mathematical spherical cap cutout from an upper surface of the holding plate, and wherein each tube slot has a retention detent between the perimetral edge and the divot.

2. The syringe and tube organizer of claim 1, wherein each retention detent is approximately midway between the perimetral edge and the divot.

3. The syringe and tube organizer of claim 2, wherein the tube slot is linear.

4. The syringe and tube organizer of claim 3, wherein the opposing chamfers are 45 degrees.

5. The syringe and tube organizer of claim 3, further comprising a connection element along a surface of the mounting plate opposite the holding plate.

6. The syringe and tube organizer of claim 5, wherein the plurality of tube slots comprising two tube slots on each side of the syringe-receiving opening, wherein the syringe-receiving opening is centrally disposed along the holding plate.

* * * * *